United States Patent [19]

Alt

[11] Patent Number: 4,782,836

[45] Date of Patent: * Nov. 8, 1988

[54] RATE ADAPTIVE CARDIAC PACEMAKER RESPONSIVE TO PATIENT ACTIVITY AND TEMPERATURE

[75] Inventor: Eckhard Alt, Munich, Fed. Rep. of Germany

[73] Assignee: Intermedics, Inc., Angleton, Tex.

[ * ] Notice: The portion of the term of this patent subsequent to Aug. 25, 2004 has been disclaimed.

[21] Appl. No.: 82,598

[22] Filed: Aug. 7, 1987

Related U.S. Application Data

[63] Continuation-in-part of Ser. No. 747,111, Jun. 20, 1985, Pat. No. 4,688,573.

[51] Int. Cl.[4] .............................................. A61N 1/36
[52] U.S. Cl. .............................................. 128/419 PG
[58] Field of Search .................. 128/419 PG, 784–786

[56] References Cited

U.S. PATENT DOCUMENTS

| | | | |
|---|---|---|---|
| 3,867,950 | 2/1975 | Fischell | 128/419 PG |
| 4,140,132 | 2/1979 | Dahl | 128/419 PG |
| 4,428,378 | 1/1984 | Anderson et al. | 128/419 PG |
| 4,436,092 | 3/1984 | Cook et al. | 128/419 PG |
| 4,503,857 | 3/1985 | Boute et al. | 128/419 PG |
| 4,535,774 | 8/1985 | Olson | 128/419 PG |
| 4,543,954 | 10/1985 | Cook et al. | 128/419 PG |
| 4,566,456 | 1/1986 | Koning et al. | 128/419 PG |
| 4,600,017 | 7/1986 | Schroeppel | 128/784 |
| 4,688,573 | 8/1987 | Alt | 128/419 PG |

FOREIGN PATENT DOCUMENTS

2609365 8/1977 Fed. Rep. of Germany ...... 128/419 PG

*Primary Examiner*—William E. Kamm
*Attorney, Agent, or Firm*—Leitner, Greene & Christensen

[57] ABSTRACT

A stimulus generator for a stimulation rate-adaptive cardiac pacemaker has a detector for sensing a first physiological parameter in the pacemaker patient, selected on the basis that heart rate is a function of that parameter, such as central venous blood temperature, and another detector for sensing a second physiological parameter in the patient representative at any given time of either patient activity or patient inactivity, such as a motion sensor. Two different algorithms are stored relating heart rate to the first physiological parameter, one for patient inactivity and the other for patient activity, in which the activity algorithm specifies a greater rate of change of heart rate than that specified by the inactivity algorithm relative to a unit change of said first physiological parameter. A decision rule is implemented based on the measurement of the second physiological parameter, by which a decision is to be made for selecting between the two different algorithms. Logic circuitry is responsive to detection of a change of the second physiological parameter to apply the decision rule to select between the two algorithms, for controlling the rate at which stimuli are generated by the stimulus generator according to the selected algorithm, and thereby, according to a heart rate physiologically appropriate to the patient's state.

14 Claims, 1 Drawing Sheet

RATE ADAPTIVE CARDIAC PACEMAKER RESPONSIVE TO PATIENT ACTIVITY AND TEMPERATURE

CROSS-REFERENCE TO RELATED APPLICATIONS

This application is a continuation-in-part of the copending application of Eckhard Alt, Ser. No. 747,111, filed June 20, 1985, now U.S. Pat. No. 4,688,573, issued Aug. 25, 1987, and assigned to the same assignee as the present application.

BACKGROUND OF THE INVENTION

1. Field of the Invention

The present invention relates generally to cardiac pacemakers, and more particularly to an exercise-responsive implantable cardiac pacemaker in which the stimulation rate is adaptively regulated according to the blood temperature of the pacemaker patient.

2. Prior Art

In situations where the natural pacemaker or pacing system of a patient's heart is disturbed because of age, disease or injury, it is customary to employ artificial pacing of the heart by implanting a cardiac pacemaker. In an atrial-triggered pacemaker, the P-wave generated preceding atrial contraction is detected to initiate the delivery of a pacing stimulus to the ventricle. It has been found that an atrial-triggered pacemaker is, to an extent, responsive to physical exertion of the patient, unlike the conventional fixed-rate pacemaker. However, in many cardiac patients, such as those suffering from atrial flutter, fibrillation, or sick-sinus syndrome, P-wave generation is not responsive to physiological conditions. Hence, the exercise-responsive advantage of atrial triggered pacemakers is not available to such patients.

In the past, many proposals have been advanced for adapting the pacemaker stimulation rate to patient exercise using a detected biological signal. Biological parameters proposed as suited for exercise-responsive adjustment of pacing rate include, for example, the pH value of the venous blood, the central venous oxygen saturation, the respiration rate, the Q-T interval (i.e., the interval from ventricular depolarization to repolarization), and the central venous blood temperature.

Cardiac pacemakers using the respiration rate or the Q-T interval for pacing rate control are currently in development and/or undergoing clinical testing. However, the use of the Q-T interval can easily cause oscillations, and thus, pacemaker-triggered tachycardia. Furthermore, the parameter these devices employ for rate control makes them particularly subject to disruption by medications currently in use to act on the electrolyte or membrane metabolism, such as beta-blocking agents, diuretics, antiarrhythmics, and digitalis.

As pointed out in patent No. OS 26 09 365 of the Federal Republic of Germany, dated Sept. 8, 1977, the central venous blood temperature may serve as a biological parameter for controlling or regulating the stimulation rate of a rate-adjustable cardiac pacemaker. A temperature-controlled pacemaker as described in that patent has not, to my knowledge, heretofore been used in actual practice. It does not offer the advantage of employing a relatively small and simple temperature sensor that may be incorporated in the catheter lead in proximity to the pacing electrode. The aforementioned publication proposes that the stimulation rate be adjusted in parallel with the blood temperature; that is to say, a rise in blood temperature would provide a correspondingly higher stimulation rate, not excluding a linear dependency between the two in an exemplary partial range of from 37° to 39° C.

A similar rate-adaptive pacemaker which depends on central venous blood temperature has been proposed in U.S. Pat. No. 4,436,092. According to the latter, a particular exercise algorithm is set forth, based on an observed mathematical relationship between blood temperature and heart rate in a normally functioning heart under stress, employing constants derived from experimental data obtained on the specific patient. The designated algorithm is utilized in conjunction with a signal obtained using a thermistor which is positioned in the patient's heart in a manner simiar to that of the German Pat. No. 26 09 305, to control the pulse frequency of the pacemaker's pulse generator. This type of control is not materially different from the control principle proposed in the German Pat. No. 26 09 305, and neither of these approaches provides true physiological adaptation of stimulation rate according to the condition of physical exertion or lack of exertion of the cardiac pacemaker patient. For example, the system proposed in the aforementioned U.S. Pat. No. 4,436,092 while not altogether clear, provides only a single algorithmic relationship between stimulation rate and instantaneous blood temperature. In U.S. Pat. No. 4,543,954, the same patentees of the U.S. Pat. No. 4,436,092 again propose a unitary algorithm relating heart rate to blood temperature, but in which the control algorithm produces abrupt jumps between two or three discrete stimulation rates for rest and exercise, depending on the sign of the derivative of temperature with respect to time relative to designated set points. Here again, the pacemaker operation does not result in stimulation of the heart in a manner corresponding to the normal physiological response.

3. U.S. Pat. No. 4,688,573

The invention disclosed in my aforementioned application Ser. No. 747,111, now U.S. Pat. No. 4,688,573 ("the '573 patent") provides a temperature-driven rate-responsive cardiac pacemaker implemented to distinguish between the physiologically determined changes of blood temperature occurring when the patient is in a resting state and those occurring when the patient is undergoing physical exertion, and to adaptively vary the stimulation rate based on change in blood temperature but according to either of two distinct and different relationships the selection of which depends on whether or not the temperature change is attributable to exercise.

My experimental data involving a multiplicity of healthy persons led me to conclude that changes in the blood temperature and in the heart rate of the individual undergoing physical stress exhibit substantially parallel behavior, independent of the individual's short-term working capacity. Therefore, rate-responsive cardiac pacing based on the blood temperature should fulfull the following conditions:

1. a definite correlation between blood temperature and heart rate, which may be assumed to be substantially linear; and 2. an intra-individual reproducibility of this correlation, since the ratio of blood temperature to heart rate appears to a large extent to be independent of the individual's working capacity.

The blood temperature is readily and consistently measured with long-term precision using known high sensitivity temperature sensors, such as thermistors or semiconductor chip thermistors. A temperature sensor has the further advantages of being of extremely small size and low energy dissipation, making it well suited for incorporation into the lead or electrode assembly of an implantable cardiac pacemaker.

Changes in blood temperature during periods when the individual is inactive, occurring, for example, with fever, ovulation, or during the normal circadian cycle, are accompanied by changes in heart rate in normally healthy persons as well as in pacemaker patients. The correlation between changes in blood temperature and heart rate in the resting state of an individual is different from that existing when the individual is undergoing physical stress.

The invention disclosed in the '573 patent, in one aspect, recognizes the problem of differentiating between physiologically determined changes of blood temperature occurring during states of rest and physical exercise of the individual; and that a solution to the problem is needed to achieve adequate adaptation of the pacing rate with change of blood temperature according to whichever of those states is at hand. The solution permits the stimulation rate to be adapted to the particular physiological condition of the pacemaker patient.

According to an important feature of the invention disclosed in the '573 patent, the cardiac pacemaker employs means for distinguishing between a rise in the individual's blood temperature owing, say, to the normal stress of his walking up a flight of stairs and that owing to the onset of fever. More particularly, there is an evaluation of the nature of the increase (or decrease) in blood temperature over a predetermined time interval to determine its physiological origin, and a consequent selective adjustment of the pacing rate based on instantaneous blood temperature according to whether the origin lies in exercise or in the normal changes that may occur during a state of rest. According to an embodiment of that invention, this is achieved in part using a field of characteristic curves, each of which is representative of the normal dependence of heart rate on blood temperature for a specified physiological condition, storing the set of curves in a matrix memory, and controlling the stimulation rate based on blood temperature according to the correlation therebetween exhibited by the curve(s) selected in response to the determination of the attributable physiological condition.

According to a preferred embodiment of the invention described in the '573 patent, a single basic characteristic curve (hereinafter called the "basic curve" or "resting curve") is selected as representative of the correlation between changes in absolute blood temperature and heart rate within a selected range under substantially any physiological condition in which physical stress is not a determining factor. Such a curve is representative, then, of the temperature change attributable, for example, to fever or to the normal circadian cycle. A typical example of circadian rhythm-based change is the decrease in blood temperature and heart rate accompanying sleep. While blood temperature change (increase or decrease) of about 0.5° C. occurs at night, and such change is also observed with exercise, the nightime changes occur slowly compared with the exercise changes.

The preferred embodiment of the '573 patent further employs a set of characteristic curves which correlate changes of blood temperature and heart rate within the aforementioned selected range under conditions of physical stress (these curves hereinafter called "exercise curves"). The exercise curves are individually selected for controlling the stimulation rate (in switching from control according to the basic curve) when the rate of change of blood temperature over a preset time interval exceeds a predetermined value. For example, selection of an exercise curve for pacing rate control may be based on an increase of at least 0.04° C. per minute in the patient's blood temperature.

Thus, if the cardiac pacemaker is functioning according to the basic curve, a measurement of absolute blood temperature along that curve corresponds to a distinct heart rate, and the stimulation rate of the pacemaker is controlled accordingly. For example, a heart rate of about 70 beats per minute (bpm) will typically accompany a central venous blood temperature of 37° C., while an elevated heart rate of, say, 95 bpm will accompany a fever temperature of 38.5° C. In both cases, the cardiac pacemaker patient is in a resting condition, which is identifiable by the absence of a time rate of change of his blood temperature in excess of the predetermined value. Hence, the stimulation rate remains under the control of the basic curve, close to the rate also observed in healthy persons.

If the patient now physically exerts himself, his blood temperature will increase per unit time at a rate significantly higher than any increase which might normally occur in the resting state during the same time interval. If that time rate of change exceeds the predetermined value (which is selected to be commensurate with any condition of exercise), the cardiac pacemaker thereupon switches functioning modes from the basic curve to the applicable exercise curve, such that the stimulation rate is regulated according to the latter curve. Since blood temperature increases with the amount of physical exercise by the individual patient, the pacing rate, controlled by temperature increase, will also increase according to the extent of exercise.

When the patient ceases the physical exertion his blood temperature will drop, which produces an adjustment of the stimulation rate of the pacemaker in the form of a decrease according to the respective exercise curve. The pacemaker continues to function in this manner until the decrease of blood temperature per unit time reaches a predetermined lower limit indicative of more gradual change or no further significant change. At that point, the reduced rate of change of blood temperature with time is indicative of the patient being in a resting state, and the pacemaker's temperature-driven rate-responsive function commences a return to the basic curve in a manner avoiding any abrupt change in the patient's heart rate.

According to another aspect of the invention disclosed in the '573 patent, a period of time is selected as a further criterion for predetermining the point at which the pacemaker's stimulation rate adjustment function changes from control according to an exercise curve to that of the basic curve. This period may, for example, range from a few minutes to an hour. In any case, it should be chosen to reflect a time interval following which, if no significant variation has occurred in the rate of change of the patient's blood temperature, it is appropriate to return to reliance on the basic curve for stimulation rate control. In the preferred embodiment of that invention, this period is chosen to have a duration of thirty minutes. These criteria serve to place a limit on the incidence of any pacemaker-mediated tachycardia. Of course, if the patient if actually undergoing physical stress for a longer time, there will continue to be a significant relative change in measured temperature per preselected time interval (that is, rate of change of blood temperature with time), and accordingly the adjustment of pacing rate will continue to be controlled according to the exercise curve.

If the patient is subjected to consecutive intervals of increasing and decreasing physical stress over a relatively long period, as might occur, for example, in the course of a long walk or light hike, it is possible ultimately to achieve a metabolic state of balance (i.e., equilibrium, or a steady state), where heat production equals heat loss, and in which the pacemaker follows the different metabolic conditions over a lengthy time interval with the respective adequate new rate. According to a further aspect of the invention disclosed in the '573 patent, logic circuitry of the cardiac pacemaker is implemented to recognize the existence of such a steadystate condition, and should it continue over the entire duration of the aforementioned selected period—say, thirty minutes—to use this as a criterion for returning control of the pacing rate to the basic curve. The pacemaker circuitry is arranged to initiate a program of transition by which the pacing rate is reduced in a physiologically appropriate manner.

It follows that in the case of a long-lasting exercise, cardiac output may decrease with this reduction in stimulation rate. However, if the patient continues to undergo physical stress, with the continuing heat production his body will react with a new increase in blood temperature. This is caused by the more limited ability to dissipate the same amount of heat by maintaining the same blood skin circulation with lower heart rate, if the decrease in pacing rate leads to a lower cardiac output. Consequently, the pacemaker rate adjustment control will revert again from the basic curve to the applicable exercise curve, following this new increase in blood temperature. On the other hand, if the patient's blood temperature does not undergo significant rate of change with time after reaching the steady-state condition, the adjustment of pacing rate will continue in accordance with the basic curve.

The course (i.e., rate of change, or slope) of each of the characteristic curves may be freely selected, provided that this slope is adapted to the physiological conditions of the pacemaker patient. In particular, the curves may be linear, with the slope of the exercise curve set, for example, from 40 to 120 bpm per degree Centigrade, and the slope of the resting curve set, for example, from 5 to 25 bpm per degree Centrigrade. For most cardiac pacemaker patients, the slope is most appropriately set or near the midpoint of these exemplary ranges, viz., 80 bpm/°C. for exercise and pb 15 pk bpm/°C. for rest. At the higher end of the blood temperature range, the curves may have a decreasing slope, which better correlates to physiological conditions.

In principle, all exercise curves may be parallel to each other, for the purpose of simplifying the internal processing of the pacemaker. In that case, the adjustment of pacing rate may be carried out with only a basic curve and the exercise curves, parallel to the abscissa, displaced according to the working point of the pacemaker.

The internal circuitry for controlling stimulation rate may be programmable as to several parameters, for the purpose of adapting the control or regulation to the particular needs of the individual patient. For example, the heart rate may be programmed for a range from 50 to 180 bpm; and the measurement range of the blood temperature may be set from 36° C. to 40° C. Also, periodic measurement (i.e., sampling) of blood temperature is preferred, and may be programmed to occur more rapidly with increasing rates of change of blood temperature per unit time. This assures rapid adjustment of stimulation rate commensurate with rapid changes of blood temperature of a patient undergoing physical stress, and thereby, to the physiological condition of the patient.

Experimental results indicate that intermittent, sudden fluctuations in the blood temperature sometimes occur, perhaps arising from the patient's respiration. In any event, the effect of a false indication of sudden change in blood temperature may be minimized by adjusting such a measurement to a median, maximum or minimum value.

To assure consistent measurement of blood temperature without regard to the patient's extremities involved in the physical exertion (that is, whether the arms, the legs, or both are involved), it is necessary that the temperature sensor be positioned at a site within the heart where good mixing of the venous blood occurs, such as at or near the boundary between the atrium and the ventricle. Preferably, the sensor is located from four to eight centimeters behind the electrode tip so that it will be properly situated whether the tip is positioned in the ventricle or (in consequence of looping of the lead) in the atrium.

Thus, among other things, the invention disclosed in the application Ser. No. 747,111 provides a cardiac pacemaker in which pacing rate is adaptive to changes in central venous blood temperature, by selectively controlling the pacing rate according to one or the other of at least two algorithms representing distinct non-constant relationships between heart rate and blood temperature. Further, that invention provides a temperature-driven rate-responsive cardiac pacemaker in which stimulation rate is adjusted according to any of a plurality of distinct curves relating stimulation rate to patient temperature in a non-constant manner, the specific curve for controlling the rate adjustment being selected according to a decision rule based on time rate of change of temperature, or, stated in a slightly different manner, a decision rule based at any given time on the slope of a curve that relates the time rate of change of the blood temperature to heart rate relative to a predetermined threshold value (0.04 degrees centigrade per minute in the preferred embodiment, in the case of pacing rate control being moved from the resting curve to an exercise curve).

However, circumstances may arise in which it is preferable not to use, or at least not to rely solely upon, the slope of such a curve relative to a predetermined threshold value as the decision rule (for discriminating between resting curve and exercise curve in going from the former to the latter, or the passage of a predetermined period of time without material change as the decision rule for return to the resting curve) for selectively discriminating between the two different types of curves or algorithms at any particular point in time. Accordingly, it is a principal object of the present invention to provide a rate responsive cardiac pacemaker in which central venous blood temperature of the patient in the determining parameter for adjustment of heart rate under conditions of rest and exercise according to defined algorithms, as described in the application Ser. No. 747,111, but in which a different parameter or parametric change is utilized as a criterion or discriminator for selecting between the resting and exercise algorithms.

SUMMARY OF THE INVENTION

Briefly, according to the present invention any parameter, other than rate of change of blood temperature, suitable for discriminating between a state of non-exercise and a state of exercise of the pacemaker patient may be utilized as the basis for selecting between the resting curve and the exercise curves, each of which relates blood temperature to heart rate in a physiological manner for the respective conditions of rest and exercise. Such other parameter may, for example, be the pH level of the venous blood, the central venous oxygen saturation, the respiration rate, the QT interval, or other physiological parameter heretofore suggested or otherwise suited for the aforementioned use, or any means by which activity or movement of the patient may be sensed and applied for such purpose.

Thus, the present invention requires a second sensor for detecting a complementary parameter as the discriminator between the resting and exercise algorithms relating central venous blood temperature and heart rate. In a presently preferred embodiment of the invention, the complementary parameter is activity and the second sensor is a motion detector in the form of a mechanoelectrical converter such as a piezoelectric crystal by which a change from absence of activity to activity, or vice versa, of the patient is virtually instantaneously detected and converted into a representative electrical signal for selecting between applicable rest and exercise algorithms. The second sensor is used only for purposes of selecting between the two, either as the only or as a confirming decision rule, and thus need not be elaborate or complex as would be the case if the complementary parameter it detects were the determinant of a relationship with heart rate. Moreover, the pacemaker remains temperature driven, and this is important because experimental results have clearly shown blood temperature or a variable which is a function of blood temperature to be a reliable biological indicator of a patient's circadian rhythm, fever condition, state of physical exertion, and the like, and of the natural heart rate appropriate to the particular condition.

Accordingly, it is another object of the present invention to provide a rate responsive pacemaker in which the selection between two different algorithms relating heart rate to blood temperature, one for rest state and the other for exercise state, is accomplished by applying a decision rule based on change of a parameter other than blood temperature indicative at any given instant of time of only one of those two states, either alone or in confirmation of the rate of change of blood temperature relative to a predetermined value.

BRIEF DESCRIPTION OF THE DRAWINGS

The above and other objects, aspects and advantages of the present invention will become apparent to those knowledgeable in the field to which the invention relates, from the following detailed description of a preferred embodiment of the invention, in conjunction with the accompanying drawings in which.

DETAILED DESCRIPTION OF THE PREFERRED EMBODIMENT

Figure 1:
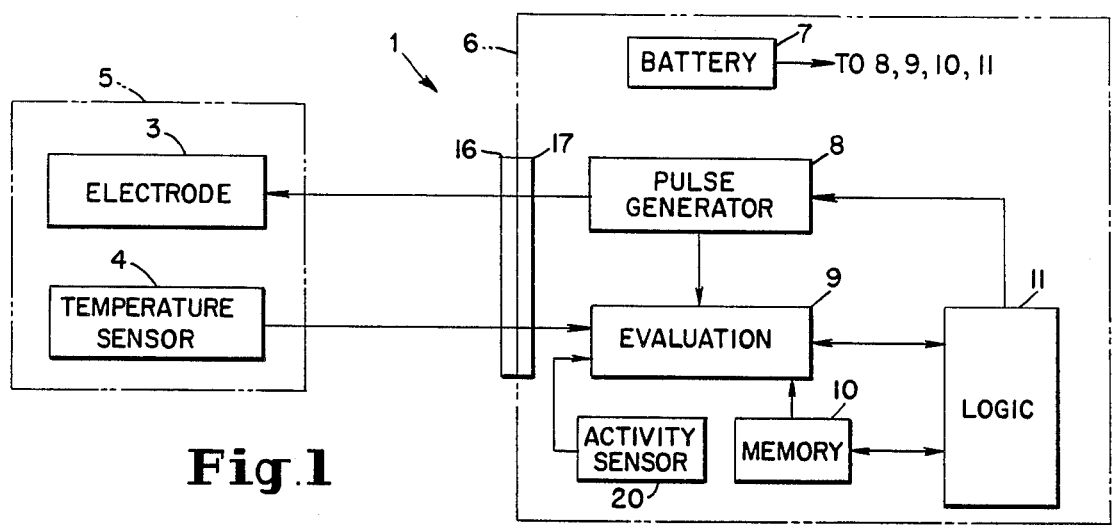
FIG. 1 is a block diagram of the preferred embodiment.

Referring now to FIG. 1, an implantable cardiac pacemaker 1 includes a lead assembly 2 (FIG. 2) having a stimulating electrode 3 at the tip thereof. A high sensitivity temperature sensor 4, preferably comprising a known thermistor, chip thermistor or other tiny, highly sensitive, low dissipation thermoelectric transducer is incorporated integrally with the lead assembly and spaced about four to eight centimeters behind the electrode tip. The electrode may be positioned within either the atrium or ventricle of the patient's heart diagrammatically represented by boundary 5. The lead assembly is configured for connection with the housing (i.e., case) 6. The latter contains a battery 7 for supplying power to the entire pacemaker, pulse generator 8 for delivering pacing stimuli to the heart via electrode 3, an evaluation circuit 9, memory circuit 10, and logic circuit 11.

Figure 2:
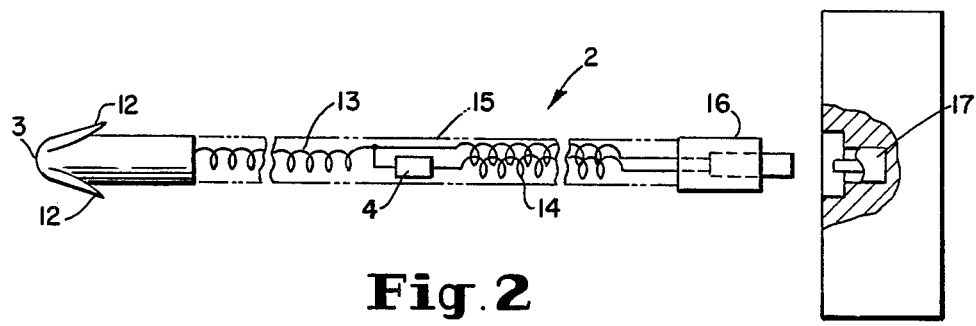
FIG. 2 is a simplified diagrammatic representation of an electrode/lead assembly arranged for unipolar stimulation and having an integral temperature sensor.

Referring now to FIG. 2, lead assembly 2 is structured for unipolar stimulation, with stimulating electrode 3 having associated therewith in proximity to its tip a set of anchoring members 12 for fixation of the electrode in proper position in the selected chamber, for example the atrium. Stimulating electrode 3 is connected to a coil 13 which may also be connected to a terminal of thermistor 4. The other terminal of thermistor 4 is connected to a second coil 14 of lead assembly 2. The coils 13 and 14 are electrically insulated from one another by suitable coverings, and lead assembly 2 is covered with a similar insulating layer 15. The lead assembly is of appropriate diameter and flexibility for conventional introduction of the electrode into the selected chamber of the patient's heart.

Coils 13 and 14 are coupled to the pacemaker circuitry within housing 6 via a male connector terminal 16 at the proximal end of lead assembly 2, which is insertable into a female connector 17 in a connector block integral with the housing. Connector terminal 16 is preferably of coaxial design and also preferably includes a reference circuit (not shown) of conventional half bridge design for calibrating the thermistor to a reference temperature. The thermistor is also connected via the reference circuit and connector 16, 17 to evaluation circuit 9.

It will be understood that other conventional connector circuits and/or configurations may alternatively be employed, the foregoing arrangement being by way of example only. This applies as well to the electrical connections to temperature sensor 4, which may for example be provided by separate insulated conductors. Moreover, the pacemaker may utilize bipolar stimulation instead of unipolar stimulation, and in that case the lead assembly 2 would include both cathode and anode at the distal end thereof.

Preferably, temperature sensor 4 has long-term stability, high sensitivity to absolute temperature and temperature change (e.g., 0.01° C.), and low energy consumption, as well as the necessary limitation on size to be accommodated in the lead assembly in the manner diagrammatically shown in FIG. 2. As noted earlier herein, such features are readily found in conventional thermistors.

Among other things, logic circuit 11 controls the interval at which the electrical signal representing the instantaneous temperature detected by sensor 4 is sampled by evaluation circuit 9 and stored in memory 10. This interval may range, for example, up to ten seconds. Evaluation circuit 9 calculates relative change between the instantaneous temperature samples and the previous samples stored in memory 10, per selected brief interval of time. Each of the evaluation circuit 9 and memory 10 is connected to logic circuit 11 by a bidirectional data bus.

According to the present invention, an additional sensor is provided to detect a complementary parameter (that is, other than blood temperature) or a function of a complementary parameter suitable to distinguish between states of rest and exercise by the patient. In the presently preferred embodiment, this additional sensor is an activity sensor 20 (FIG. 1) which is housed within the pacemaker case 6. Preferably, the activity sensor comprises a known form of miniature piezoelectric crystal in the form of a weighted cantilever arm to detect movement of the patient. A suitable form of such an element is disclosed, for example, in U.S. Pat. No. 4,140,132, but it will be understood that other known types of activity or motion sensors may alternatively be used. When the patient moves, the weighted cantilever arm undergoes vibration and the vibrations are converted to electrical signals by the piezoelectric crystal.

The output signals of the activity sensor 20 are applied to evaluation circuit 9 which, in addition to its aforementioned function relative to the sensed temperature signals, converts the activity signal to a representative digital signal for application to the logic circuit 11. In its simplest form, the activity sensor/evaluation circuit may simply provide an indication of either movement or no movement by the patient. That is to say, the presence of a signal is indicative of activity (a state of exercise) and the absence of a signal is indicative of no activity (a state of rest) of the patient. More elaborate forms of detection may include the use of a threshold detector and a timer, or other suitable means, for ascertaining sustained activity of a predetermined magnitude over a preselected minimum interval of time, to eliminate slight movements of the patient while in a resting position such as turning during sleep, or coughing. It is sufficient to note, however, that the principal purpose of the additional sensor (in this embodiment, activity sensor 20) is to provide, alone or in conjunction with a function of the sensed blood temperature, a means for implementing a decision rule by which a selection may be made between a first algorithm representative of a state of rest and a second algorithm (or set of algorithms) representative of a state of exercise of the patient, as will be discussed in detail presently.

The logic circuit 11 is also connected to pulse generator 8 for the purpose of controlling the pulse repetition frequency (i.e., stimulation rate) of the generator. This control is effected through the use of characteristic curves of the type described earlier herein, which will be further explained by reference to FIG. 3. The linear curve designated K2 represents an algorithm relating heart rate to blood temperature in a non-constant manner within an exemplary temperature range from a minimum of 36° C. to a maximum of 40° C. It will be observed from FIG. 3 that over this temperature range the locus of heart rates defining curve K2 ranges from approximately 50 to approximately 120 bpm. From the earlier description, it will be recognized that curve K2 constitutes the basic or resting curve.

Figure 3:
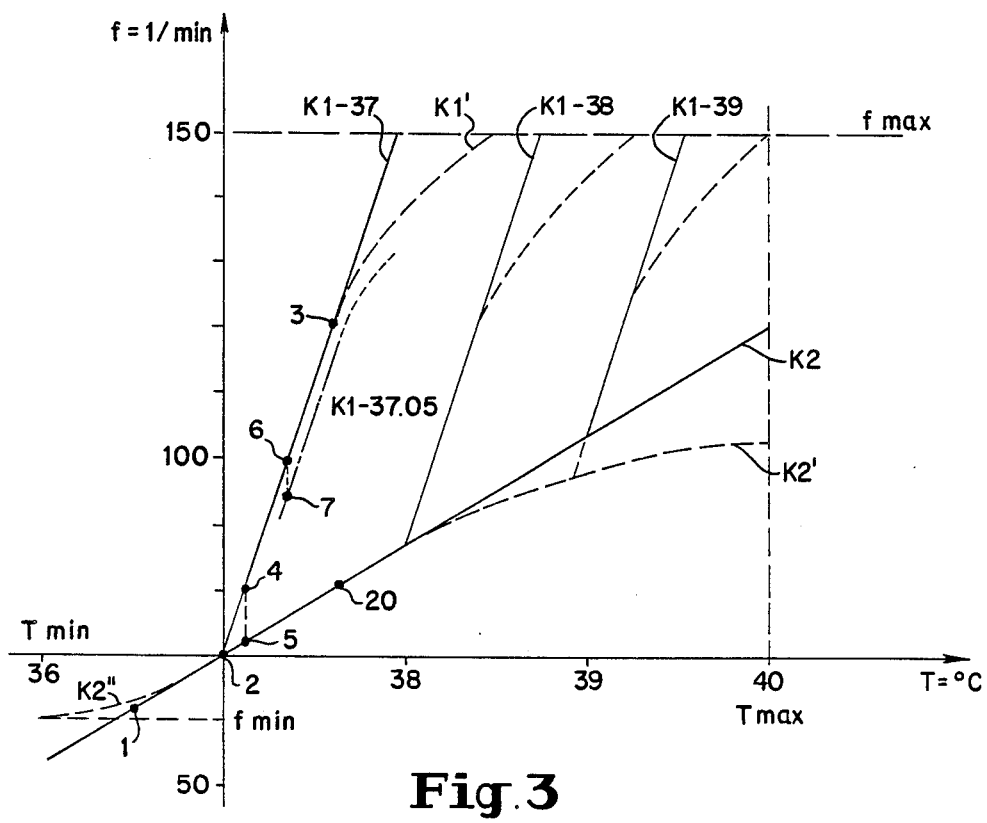
FIG. 3 is a graph of heart rate versus blood temperature for characteristic curves of the types employed in the preferred embodiment, on which a functional cycle is plotted to illustrate the mode of operation.

Superimposed on the resting curve K2 of FIG. 3 are several other linear characteristic curves designated K1-37, K1-38, and K1-39, representing at separated points of intersection with the resting curve, algorithms distinct from that represented by the resting curve and each relating heart rate to blood temperature in a non-constant manner. It will be observed that the K1 curves are parallel to one another, with a higher slope than resting curve K2. From the previous description, it will be recognized that the K1 curves constitute the exercise curves.

In particular, the K1 curves are developed to have, in this example, a linear variation of eighty beats per minute per degree Centigrade throughout (that is, to have a slope of 80 bpm/°C.). This is most readily observed in the case of exercise curve K1-37, so designated because it intersects resting curve K2 at the 37° C. mark which happens, in this example, to be at the origin of the graph. The heart rate coinciding with that point is 70 bpm. It will further be observed that the K1-37 curve "crosses" the 150 bpm "line" along the heart rate or Y-axis, at the upper end of the graph, and that this point coincides with a temperature of 38° C. along the absolute temperature or X-axis. Inasmuch as in this example, the K1-37 curve (and each of the other exercise curves) is not only linear but, indeed, a straight line, the slope of K1-37 is 80 bpm/°C. Further, since the other exercise curves K1-38 and K1-39 are parallel to K1-37, they have the same slope.

It will be understood, however, that other slopes may be utilized for all or any portion of the exercise curves while retaining linearity and a non-constant relationship between heart rate and temperature. For example, curve K1-37 may have a region of decreasing slope with higher temperatures as indicated in the graph of FIG. 3 by dotted line K1'. In that event, the other exercise curves would have corresponding regions of decreasing slope, as indicated by the respective dotted line segments parallel to K1', each such region being representative of a more gradual variation of heart rate (or, where the relationship is used for pacing control, stimulation rate) for a given change of blood temperature as compared to the variation of heart rate along the solid line segment of each exercise curve. Similarly, resting curve K2 may have a region of decreasing slope with higher temperatures as indicated by dotted line segment K2' representing a more gradual variation of heart rate relative to blood temperature than along the solid line segment of that curve. Another region of more gradual variation of heart rate with change of temperature may be provided at the other end of resting curve K1, as indicated by dotted line segment K2", constituting a region of increasing slope when viewed with increasing absolute temperature (e.g., from 36° C. to 37° C.). As noted above, such regions of more gradual variation of heart rate at the upper end of the absolute temperature range better correlate to normal physiological conditions.

The upper and lower limits of both the heart rate range and the absolute blood temperature range may be programmed in the cardiac pacemaker, thereby circumscribing the range within which the stimulation rate adjustment function of the pacemaker is adaptively controlled. Thus, in the exemplary graph of FIG. 3, the lower limit $f_{min}$ of the heart rate range is set at 60 bpm and the upper limit $f_{max}$ is set at 150 bpm. Similarly, for the absolute temperature range the lower limit $T_{min}$ is programmed to 36° C. and the upper limit $T_{max}$ is programmed at 40° C.

An exemplary cycle of operation of the rate adjustment control function of cardiac pacemaker 1 (FIG. 1) will now be described with reference to all of the Figs. of drawing, and especially FIG. 3. It will be assumed that the pacemaker is implanted in a patient, and as previously discussed, that the lead 2 has been introduced such that the stimulating electrode 3 is properly positioned in the desired chamber of the heart 5, with temperature sensor 4 situated in a region of strong mixing of the central venous blood (e.g., at the boundary between atrium and ventricle) in the right side of the heart, and that the additional sensor of a complementary physiological indicator—here, activity sensor 20—is properly implanted to detect or measure that complementary indicator of the state of rest or exercise of the patient. It will be understood that except for the specific components, including circuitry, employed for controlling the adjustment of the rate at which stimuli are delivered by the pulse generator, the pacemaker may be entirely of any conventional type (other than fixed rate, of course).

When the pacemaker patient is resting, and by that term is meant any state of substantial inactivity, whether reclining, sitting, standing or other position of the body, the stimulation rate of the pacemaker (that is, the pulse repetition frequency of pulse generator 8, under the control of logic circuit 11) is controlled according to the resting curve K2. For the sake of the present example of operation, it will be assumed that the patient is sleeping. Hence, activity sensor 20 produces no output signal, inasmuch as there is no movement of the patient, or, if there is some movement (as in the case of a change of position of the sleeping patient, or even in the case of fitful sleep by the patient) it is not sufficiently pronounced and sustained to generate an activity output signal from evaluation circuit 9. At the same time, instantaneous temperature measurements from the output waveform of sensor 4 are sampled by evaluation circuit 9 under the control of logic circuit 11, and each new sample is compared to the prior sample stored in memory 10 to determine the rate of change of the blood temperature per sampling interval. In the case of a resting patient, this time rate of change of blood temperature will be less than the predetermined threshold level at which the evaluation circuit has been programmed.

Evaluation circuit 9 generates an output which is indicative of an absence of output signal from the activity sensor 20 (e.g., by virtue of a lack of pronounced and sustained activity of the patient to reach or exceed threshold for the prescribed period of time). If desired, it may also provide an output based on the time rate of change of blood temperature relative to the threshold value for time rate of change of temperature for selection purposes. In the latter instance, the time rate of change of blood temperature could be used as a confirming or separate decision rule by which to select pacing rate as a function of the central venous blood temperature according to whether the patient is exercising or at rest. However, for purposes of the preferred embodiments, only the indication provided by the additional sensor 20 is used for the algorithmic curve selection decision. Logic circuit 11 is responsive to the output level of the evaluation circuit, based on the output of the activity sensor 20, to continue normal control of the output pulse rate of pulse generator 8 according to the resting curve K2 stored in memory 10, that is, according to the predetermined relationship between heart rate and blood temperature of a healthy person represented by the resting curve.

Upon waking from the night's sleep, the patient's blood temperature is typically approximately 36.5° C. and his heart rate at that point is (or, as a result of the control exerted by logic circuit 11 on the stimulation rate of generator 8, is paced to be) approximately 60 bpm (point 1 on basic curve K2). With the daily rhythmic cycle constituting the individual's circadian rhythm, the patient's blood temperature ultimately rises to 37° C., and the heart rate (again, as necessary, by adaptation of stimulation rate through operation of the adjustment system) increases to 70 bpm (point 2 on basic curve K2, at the origin of the FIG. 3 graph). If the patient remains in a state of rest, the activity sensor 20 will so indicate by the absence of an output signal, indicative of either no movement or insufficient movement of the patient to produce a change of control by the logic circuit 11. (Also, his blood temperature will rise or fall only slightly, if at all, per unit time represented by the blood temperature sampling interval). Consequently, the internal logic circuit 11 maintains control of the pacing rate according to the stored resting curve K2.

When the patient awakens and commences physical activity, for example getting up from the bed and walking across the room, activity sensor 20 instantaneously generates a sustained output signal as the weighted cantilever arm undergoes continuous vibration and causes the piezoelectric crystal to generate an electrical output representative of sustained activity of the patient equal to or exceeding a predetermined magnitude. This constitutes the criterion or decision rule that the patient has undergone a change of state, in this example from rest to exercise, and that determination is communicated instantaneously to the logic circuit which thereupon switches control of the pacing rate according to the applicable exercise curve K1. If the blood temperature at that moment were 37° C., the shift would be from resting curve K2 to exercise curve K1-37 since the current working point of the pacemaker is at the absolute blood temperature at the intersection of those two curves.

Assume that the blood temperature now rises to about 37.6° C. (point 3 on curve K1-37) as a consequence of the patient's physical exertion, in which event the stimulation rate is adaptively adjusted to approximately 120 bpm. When the patient ceases his physical exercise, the activity sensor 20 will cease generating an output signal, and the control of pacing rate would then be returned toward the resting curve K2, according to that decision rule. At that time, the working point of the pacing rate control, as manifested by the logic circuit, will proceed along exercise curve K1-37 as the patient's blood temperature drops, until the time rate of change of the blood temperature drop is less than a preset threshold level programmed in the evaluation circuit 9 (e.g., at a relatively steady temperature of 37.1° C. and a stimulation rate of approximately 80 bpm, at point 4 along curve K1-37). The evaluation circuit generates an output level indicative of that occurrence, and the logic circuit responds by reducing the pacing rate along that temperature "line", to more rapidly shift control of the rate in a smooth transition back to the resting curve K2 (point 5, where the rate is about 72 bpm).

If, at point 4 along exercise curve K1-37, the patient resumes exercise, sensor 20 generates an output indicative of exercise, and evaluation circuit 9 and logic circuit 11 respond by shifting control of the stimulation rate back curve K1-37. As the patient's central venous blood temperature rises with the continuing exercise, the pacing rate increases according to the algorithmic relationship defined by that curve. Assume that the blood temperature and pacing rate again reach point 3 on the curve, and that the patient's activity is thereupon ceased once again. If the blood temperature thereafter drops back only to a value of 37.4° C., at point 6, and the time rate of change of the temperature drop is then less than the aforementioned preset threshold level of the evaluation circuit (for example, the temperature may be slightly elevated by virtue of the patient's circadian rhythm), the logic circuit will thereupon shift the control of the rate in a smooth transition directly back to the resting curve K2, rather than continuing the rate along curve K1-37.

In the graph of FIG. 3, this is indicated by the dotted line segment running from point 6 on exercise curve K1-37, along the 37.4° C. temperature line, to a point 7 at which the stimulation rate is 95 bpm. As discussed above, the set of exercise curves may be extensive, limited only by memory capacity and logic capability within the pacemaker's internal circuitry. Hence, numerous additional exercise curves K1 may be utilized, all of which are relatively equally spaced from and parallel to one another. In FIG. 3, the point 7 lies along an exercise curve designated K1-37.05 which, like each of the other exercise curves, constitutes an algorithm in which stimulation rate is a non-constant function of blood temperature, having a steep slope relative to the resting curve K2 and commencing from the point of intersection of the respective exercise curve with curve K2.

Should the patient resume physical exercise at point 7, the activity sensor 20 will detect this change of state and provide an output indicative thereof to the evaluation circuit. In response to the digital signal generated by the evaluation circuit, logic circuit 11 will control pulse generator 8 to adjust the pacing rate along the exercise curve K1-37.05, according to the rising temperature of the central venous blood.

Ultimately, when the patient returns to a resting condition and the working point of the stimulation rate control returns to the resting curve K2, the working point will move upwardly and downwardly along that curve with variations of the patient's blood temperature and the stimulation rate of the pacemaker will be adjusted accordingly.

Although a specific preferred embodiment of the invention has been described herein, variations of that embodiment will become readily apparent to those skilled in the field to which the invention pertains from a reading of the foregoing description, without departing from the concepts of the invention. Accordingly, it is intended that the present invention be limited only by the appended claims.

What is claimed is:

1. An implantable cardiac pacemaker for adaptively varying the heart rate of a patient according to whether the patient is resting or undergoing exercise, comprising
   first sensing means for measuring the blood temperature of the patient and for generating a signal representative of that instantaneous temperature,
   second sensing means for detecting a physiological parameter of the patient other than blood temperature indicative of whether the patient is then in a state of rest or a state of exercise and for generating a signal representative thereof,
   means storing separate mathematical relationships between heart rate and blood temperature having, respectively, a rate of change in the range from 5 to 25 beats per minute per degree C representing rest state of the patient, and a rate of change in the range from 40 to 120 beats per minute per degree C representing exercise state of the patient, and
   means responsive to the signals generated by the first and second sensing means for stimulating the patient's heart rate according to one of the stored rest state and exercise state relationships between heart rate and blood temperature selected based on whether said determination is that the patient is then in the rest state or in the exercise state.

2. The cardiac pacemaker of claim 1, in which said second sensing means comprises an activity sensor for detecting the presence or absence of pronounced sustained movement of the patient.

3. The cardiac pacemaker of claim 1, in which said stimulating means includes means for producing a smooth transition between the pacing rates at which the patient's heart is stimulated in the rest and exercise states.

4. The cardiac pacemaker of claim 3, in which
   said stimulating means further includes programmable means for preselecting a value for minimum relative change in blood temperature with time, and
   said means for producing a smooth transition includes means for shifting the control of stimulation from said exercise state relationship directly to said rest state relationship in response to a relative change of the blood temperature measured by said sensing means which is less than said preselected value.

5. A cardiac pacemaker for delivering electrical stimuli to a patient's heart, comprising
   means for generating electrical stimuli at a periodic rate,
   first means responsive to the temperature of the patient's central venous blood temperature for producing a signal representative thereof at a given point in time,
   second means responsive to the state of physical activity of the patient for producing a signal therefrom indicative of whether the patient is then at rest or undergoing exercise,
   means providing a first continuous function relating stimulation rate to measured blood temperature for a resting state and providing a second continuous function relating a faster rate of change of stimulation rate to a measured unit of blood temperature for an exercise state than that of said first continuous function, and
   means responsive to the signals produced by said first and second means for regulating the rate at which said electrical stimuli are generated by said generating means according to both the instantaneous measurement of the patient's blood temperature and the indicated state of the patient, commensurate with said first continuous function when the patient is indicated to be resting and commensurate with said second continuous function when the patient is indicated to be undergoing exercise.

6. The pacemaker of claim 5, in which
said rate regulating means includes means for producing a gradual transition between the rates at which said electrical stimuli are generated when the patient undergoes transition from a resting state to an exercise state and vice versa.

7. The pacemaker of claim 6, in which
said means for producing a gradual transition includes
means for establishing a predetermined value representing minimum change of blood temperature with time, and
means for smoothly returning the rate at which electrical stimuli are generated under regulation by said second continuous function to a rate regulated by said first continuous function upon a measured change of blood temperature which is less than said predetermined value.

8. A stimulus generator for a stimulation rate-adaptive cardiac pacemaker, comprising
means for detecting a first physiological parameter in a pacemaker patient, said first physiological parameter being selected on the basis that heart rate is a function thereof,
means for detecting a second physiological parameter in the patient representative at any given time of either patient activity or patient inactivity,
means storing two different algorithms relating heart rate to said first physiological parameter, one for patient inactivity and the other for patient activity, in which the activity algorithm specifies a greater range of change of heart rate than that specified by the inactivity algorithm relative to a unit change of said first physiological parameter,
means for implementing a decision rule based on the measurement of said second physiological parameter, by which a decision is to be made for selecting between said two different algorithms,
means for controllably generating electrical stimuli at a variable rate, and
means responsive to detection of a change of said second physiological parameter to apply said decision rule to select between the two algorithms, for controlling the rate at which stimuli are generated by said controllable generating means according to the selected algorithm, and thereby, according to a heart rate physiologically appropriate to the patient's state.

9. The stimulus according to claim 8, wherein
said means for detecting said first physiological parameter comprises means for detecting central venous blood temperature of the patient.

10. The stimulus generator according to claim 9, wherein
said means for detecting said second physiological parameter comprises means for detecting the presence and absence of pronounced sustained movements of the patient.

11. A method for pacing the heart rate of a cardiac patient, comprising
measuring the patient's absolute blood temperature at successive points in time,
relating desired pacing rate to blood temperature according to an algorithm characterizing a matabolic state of the patient representing physical inactivity, and also according to an algorithm characterizing a metabolic state of the patient representing physical activity, the two algorithms differing in rate of change of pacing rate relative to unit change of blood temperature,
pacing the patient's heart at a selectively variable rate,
measuring over time a second physiological indicator of instantaneous patient activity and inactivity,
selecting one of the algorithms at any of said points in time based on the then-current measurement of said second physiological indicator, the activity algorithm being selected when said measured second physiological indicator is indicative of patient activity and the inactivity algorithm being selected when said measured second physiological indicator is indicative of patient inactivity, and
adjusting the pacing rate under the control of the selected algorithm.

12. In a cardiac pacemaker having control means for automatic adaptation of the stimulation rate of the pulse generator of the pacemaker to the metabolic state of the patient, in which the control means includes temperature sensor means, a pacing lead coupling a stimulation electrode to the pulse generator, the temperature sensor means being situated in the pacing lead in proximity to the stimulation electrode for measuring the temperature of blood returned to the patient's heart from the musculature, and circuit means connected to the sensor means and to the pulse generator for adjusting the stimulation rate according to the measured blood temperature, the improvement comprising:
means for storing a basic algorithm and an exercise algorithm representing different predetermined relationships between heart rate and blood temperature for a normal human heart when the individual is at rest and undergoing exercise, respectively,
means for detecting an indicia of patient exercise separate from blood temperature, and
means coupled to said detecting means, said sensor means, and said pulse generator to adjust said stimulation rate according to the blood temperature measured by said sensor means and responsive to the indication by said detecting means of patient exercise or lack of exercise for selectively designating said exercise algorithm or said basic algorithm as the criterion for the adjustment.

13. The improvement according to claim 12, wherein
said detecting means comprises means for detecting an indicia which produces a faster response to patient exercise than does blood temperature.

14. The improvement according to claim 12, wherein
said detecting means comprises means for detecting patient activity.

* * * * *